United States Patent [19]

Matrullo

[11] 4,182,335
[45] Jan. 8, 1980

[54] ANAL FILTER

[76] Inventor: C. James Matrullo, 242 B Jefferson Ct., Lakewood, N.J. 08701

[21] Appl. No.: 819,542

[22] Filed: Jul. 27, 1977

[51] Int. Cl.² ............................................. A61F 5/44
[52] U.S. Cl. .................................. 128/290 R; 128/283
[58] Field of Search ............... 128/290 H, 290 R, 284, 128/287, 155, 156

[56] References Cited

U.S. PATENT DOCUMENTS

| | | | |
|---|---|---|---|
| 2,629,381 | 2/1953 | Brown | 128/290 R |
| 2,682,875 | 7/1954 | Brown | 128/290 R |
| 2,742,042 | 4/1956 | Flanders | 128/290 R |
| 2,771,882 | 11/1956 | Leupold | 128/290 R |
| 2,858,830 | 11/1958 | Robins | 128/155 UX |
| 2,964,039 | 12/1960 | Johnson, Jr. et al. | 128/200 |
| 3,039,893 | 6/1962 | Baningan, Jr. et al. | 128/155 |
| 3,199,945 | 8/1965 | Stutz | 128/155 |
| 4,053,053 | 10/1977 | Tumangday | 128/155 |

FOREIGN PATENT DOCUMENTS 242517  12/1925  United Kingdom ..................... 125/285

Primary Examiner—Robert W. Michell
Assistant Examiner—Milford A. Juten
Attorney, Agent, or Firm—Kenyon & Kenyon

[57] ABSTRACT

An anal filter for protecting underwear from soiling, is attached to a person's anus solely by non-adhesive adherence to the anus and adjacent portions of the buttocks, due to a facing of fluffy fibrous material, and when attached, serves as a filter by being pervious to the discharge of gas through the anus but substantially impervious to complete passage of excreta carried by the gas or remaining on the anus from a bowel movement. A layer may be adhesively secured to the fibrous material and which prior to use of the anal filter can be pulled off from the fibrous material while pulling this material's fibers outwardly so as to give the material its fluffy characteristic.

1 Claim, 5 Drawing Figures

ANAL FILTER

BACKGROUND OF THE INVENTION

For generations gentlemen have been embarrassed by presenting their wives or others with underwear to be washed because visibly soiled by excreta. When a prompt change of underwear has been impossible, they have been made uncomfortable by the need to wear the underwear until there is an opportunity to change. Ladies are not free from such embarrassment and discomfort.

The problem can be caused by inadequate cleaning after a bowel movement, but often it is caused by flatulence resulting in gaseous discharges through the anus. In the case of gaseous discharges, the gas may or may not carry excreta, but in any event leaves the person involved with a feeling of disquiet because it is not always possible for the person to ascertain that the gaseous discharge is clean. Although not restricted to older persons, it is they who are more apt to be troubled by such underwear staining. At the same time it is older persons who are less tolerant of correction of the problem by any device that involves application trouble and discomfort afterwards. The impatience of the younger makes them unwilling to resort to anything that cannot be done quickly.

Prior art devices offered to solve that problem have not met with wide-spread acceptance insofar as is known.

Prior art attempts to solve the problem have been along the lines exemplified by the Brown U.S. Pat. No. 3,570,489, issued Mar. 16, 1971, by which for the purpose of preventing soiling of clothing by an anal discharge, a device is offered in the form of a conical plug from the base of which a stem extends to a terminal or outer end which mounts an absorbant ball. The idea is for the user to push the plug up the anal canal so that via the stem the cotton ball is attached so as to cover the anus. The patent says that the stem must be stiff enough for insertion of the plug which holds the device in position, but flexible enough not to cause undue discomfort after the device is installed. The patent states that the user of the device will not be conscious of it, but this is believed to be very questionable. In any event, the act of inserting the anchoring plug required to hold the cotton ball protecting the anus, is sure to cause discomfort, be objectionable to any fastidious person, and must involve the use of some caution and time to which younger persons are bound to object.

Another prior art attempt to solve the problem is represented by the Davis Jr. U.S. Pat. No. 3,881,485, issued May 6, 1975. Apparently appreciating the objectionable features indicated above, in this case only the plug is used, the base of the conical plug having an indentation for the use of a person's finger, the finger being used to push the plug, which has a fibrous characteristic, up the rectum, apparently cleaning the anus as it goes to its ultimate resting place up in the anal canal. The objectionable stem of the earlier patent is eliminated but is replaced by the need for using the finger which to both ladies and gentlemen is objectionable, this being emphasized when the bowel movement occurs in a public toilet not provided with handwashing facilities.

There are earlier patents than the two specifically mentioned, but insofar as is known they all concern medication applicators as compared to something a person might use in everyday life.

Insofar as is known, no one has paid any attention to the problem involved by gaseous anal discharges which may either be clean or, and this happens often, carry at least minute quantities of excreta. With all known prior art devices, it is not understood how they permit a gaseous discharge, although such a discharge is commonly experienced by everyone, particularly after eating foods which result in gaseous discharges. Careful cleaning of the anus after a bowel movement can prevent the problem sought to be cured by inventors in the past, but the problem of underwear soiling due to gaseous discharges, which is probably more common, has not only remained unsolved, but apparently undiscussed.

DESCRIPTION OF THE INVENTION

The present invention provides for the first time an anal filter, comprising a base layer made of porous flexible material to which a fluffy non-woven fibrous layer is attached, the filter having a length sufficient to transversely extend over the anus and adjacent portions of a person's buttocks and having a width at least sufficient to cover the anus in a vertical direction. The dimensions need not be much greater than just indicated. Both of the layers are made of materials easily flexible under finger pressure so that the filter itself is correspondingly flexible and can be laid with the fibrous layer inward transversely between the buttocks and pressed inwardly by finger pressure so that by bending a generally central portion of the fibrous layer contacts the outside of the anus with the balance of the fibrous layer contacting the adjacent portions of the buttocks, the base layer, of course, bending with the fibrous layer since the two layers are interconnected. The filter may be prebent or doubled by the user prior to application or bent during the application.

Surprisingly, with the fibrous layer, preferably absorbant cotton possibly fluffed out a bit, contacting the anus and the adjacent portions of the buttocks, the filter remains attached without the use of other expedients, either plugs for anal insert, adhesive tape or the like, until physically pulled away deliberately or by a bowel movement. The fluffy material apparently has a mechanical adherence which holds the filter firmly in position during all phases of a person's normal physical activity.

Both layers are made pervious to the discharge of gas through the anus but substantially impervious to complete passage of excreta carried by the gas. The base layer may be made of woven cloth, exemplified by gauze, while the fluffy non-woven fibrous layer is inherently gas pervious. Either can carry a deodorant, but preferably the cloth layer is used for this purpose. The base layer may also be a plastic material provided with a large number of perforations. In either case the fluffy material may be fixed to the base layer adhesively providing the adhesive used does not form a gas-impervious barrier.

Preferably the filter is in the form of a strip having at least the main dimensions indicated. The filter should be made very flexible because adherence is obtained by the fluffy material and not by any springing apart of the filter after its application.

Although not indicated before, the fluffy material should preferably be sterile and ordinarily sterile absorbant cotton is suitable. The base layer preferably carries deodorant such as activated carbon, a chlorophyll material, etc., to reduce or eliminate the odor of excreta filtered and caught by the anal filter and, possibly, to deodorize clean gas passed through the filter. Maximum possible flexibility on the part of the filter is desirable.

At present it is comtemplated that for normal persons the filter may be about 2½" long and about ¾" wide, with a rectangular shape, although other shapes may be used.

In use, when a person starts out in the morning, the anal filter can be installed with one hand simply by holding the filter between the two fingers on either side of the forefinger and using the forefinger the filter can be pressed into position, although prebending of the filter by doubling it may make installation a bit easier. The action involved is quick, positive and free from disgust. Once attached, the presence of the filter cannot be detected by the person involved, because the filter is extremely flexible, gives with every motion of the body and becomes, in effect, a part of the person. The filter is undetectable during all activities, including sitting, and all the while the filter remains firmly attached and gives the person a sense of security. If gas must be discharged, the gas can pass through the filter and the filter does not blow off, but if any excreta is present in the gaseous discharge, it is caught by the cotton and filtered from the gas before the excreta can completely pass through the filter, the outside or base layer remaining clean. A person using the filter is free from worry concerning underwear soiling.

On the other hand, a person who has just had a bowel movement and who has cleaned the anus as much as possible, can with the same easy motion attach the filter and go forth serene in the knowledge that if the cleaning operation was inadvertently incomplete, no underwear soiling can occur because the filter is impervious to the complete passage of excreta.

Because the anal filter of this invention is inherently in the form of a flat device, it can be carried singly or in multiple, so that it is available for use at any time anywhere. It can be easily packaged for merchandising, preferably in sterile containers.

When carried or packaged, it might be possible for the fibrous material to become compacted to a degree preventing it from having its surprising characteristic of adherence to the person. This can be corrected by manually fluffing up the fibers of the fibrous material, but for effectiveness this depends on the skill of the user.

Therefore, according to the present invention, a layer is adhesively secured to the fibers of the fibrous material on its side that will be applied to the person. The base layer and the fibrous layer should be permanently connected together; the just-mentioned layer should be removably secured to the fibrous material as by means of a pressure-sensitive adhesive. In other words, the fibrous layer is sandwiched between two layers, the base layer and the second layer, which can be called an inner layer because it is on the inward side of the fibrous material.

The purpose of this inner layer is twofold. First, it forms the anal filter into what is, in effect, a package, the inner layer possibly carrying instructions for use of the anal filter, a trademark or other indicia. Of more importance is the fact that because this inner layer is adhesively secured to the fibers of the fibrous layer by an adhesive which permits the inner layer to be pulled free, the action involved in pulling the inner layer free to prepare the anal filter for use, inherently pulls many or all of the outermost fibers of the fibrous layer outwardly or upwardly so as to impart the previously described fluffy characteristic automatically, independent of the user's skill, and so as to provide the desired degree of fluffiness. When the inner layer is pulled away, it inherently fluffs up the surface of the fibrous material automatically. The permanent layer on the other or outer side of the fluffy material should be fixed to the fluffy material firmly enough to remain a permanent part of the filter.

Ordinarily this inner layer may also be flexible like the anal filter itself. This permits the inner layer, or protective or packaging layer, to be easily peeled away by bending and pulling of the inner layer. In some instances this inner layer may be made of relatively rigid material with the filter itself being pulled away to provide the fluffiness and prepare the filter for use.

DESCRIPTION OF THE DRAWINGS

The accompanying drawings illustrate examples of this anal filter, the various figures being as follows.

DETAILED DESCRIPTION OF THE DRAWINGS

Having reference to the above drawings, the base layer is shown at 1 as comprising in this instance a strip of gauze or its equivalent; in other words, the base layer is a loosely woven fabric which is highly permeable to the passage of gas and which is as flexible as possible. The fluffy non-woven fibrous material is shown at 2 attached to the base layer 1 and substantially thicker than the base layer. The fluffy material is preferably sterile absorbent cotton, and in any event, should not be highly compacted because the fluffy nature provides for the attachment to the person and for gas perviousness. At the same time the fluffy layer should be thick enough to provide for what the general filter industry calls depth filtration.

As previously indicated, the filter dimensions presently considered preferable are represented by 2¼" length and a ¾" width, these dimensions being subject to variation providing the purpose and function of the filter is retained.

Figure 1:
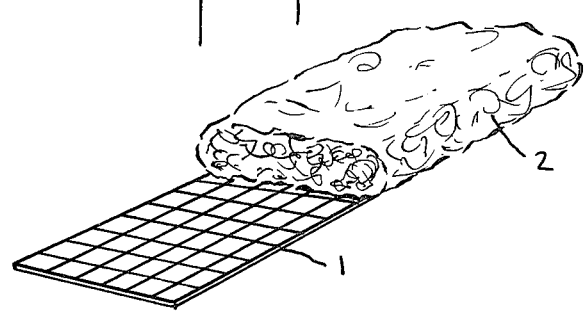
FIG. 1 is a perspective view showing the anal filter with the fluffy material cut away to reveal the base layer.
Figure 2:
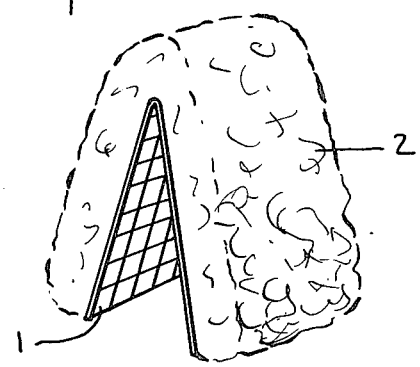
FIG. 2 shows the easy bendability of the filter to the condition it acquires when attached to the person.

In FIG. 2 the foldline of the bent filter is shown as being suitable for persons who do not have fat buttocks. The filter may be more sharply bent in the case of obese persons, and possibly it may be made and sold in a doubled condition.

Figure 3:
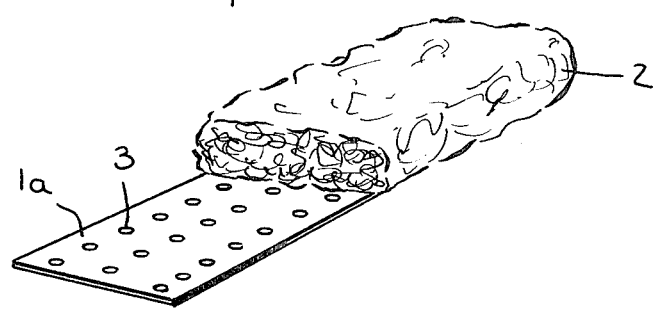
FIG. 3 is like FIG. 1 but shows a modification.

In FIG. 3 the same parts are shown excepting that the base layer 1a is illustrated as being made of plastic having a large number of perforations indicated at 3. In this case also the filter is gas pervious but impervious to complete passage of excreta, and it also should be relatively flexible.

In addition to the installation of the filter as previously described, when the filter is sharply bent it is not necessary to press its central portion against the anus by using direct finger pressure in that area. Although flexible, and depending on the condition of the buttocks, the folded filter may possibly be simply pushed into the crack between the buttocks so that its central portion contacts the anus, the fluffy material then holding the filter firmly attached.

It can be seen from the foregoing that this invention provides for something that has long been overlooked, namely, a filter which filters excreta possibly carried by gaseous anal discharges while at the same time protecting underwear against an incompletely cleaned anus after bowel movement. The device is applied about as quickly as can be imagined, no application skill is involved, and when once applied, the wearer is completely unconscious of the presence of the filter.

Gaseous discharges do not detach this filter; only physical pulling or a bowel movement can detach the filter.

Figure 4:
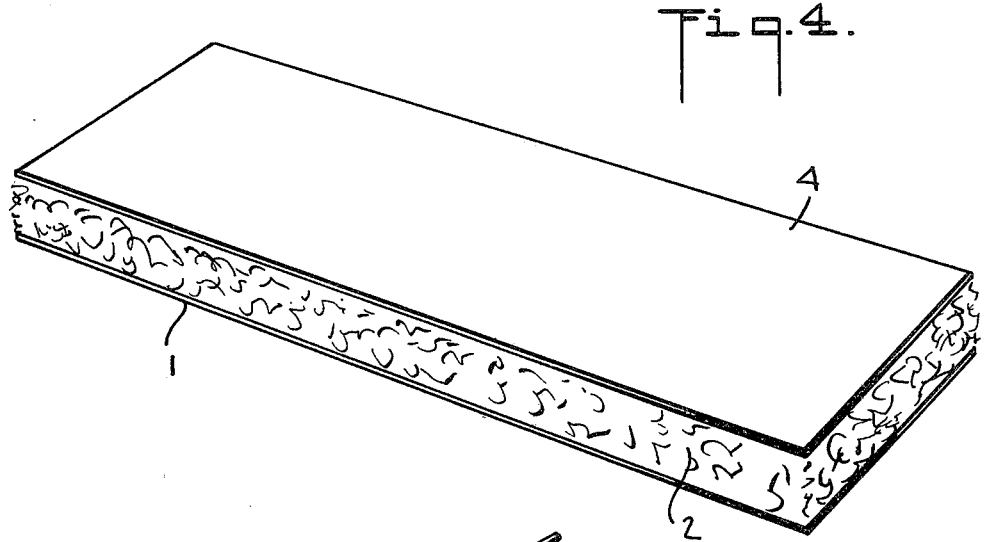
FIG. 4 is a perspective view showing the anal filter having the previously described inner or protective or packaging layer.
Figure 5:
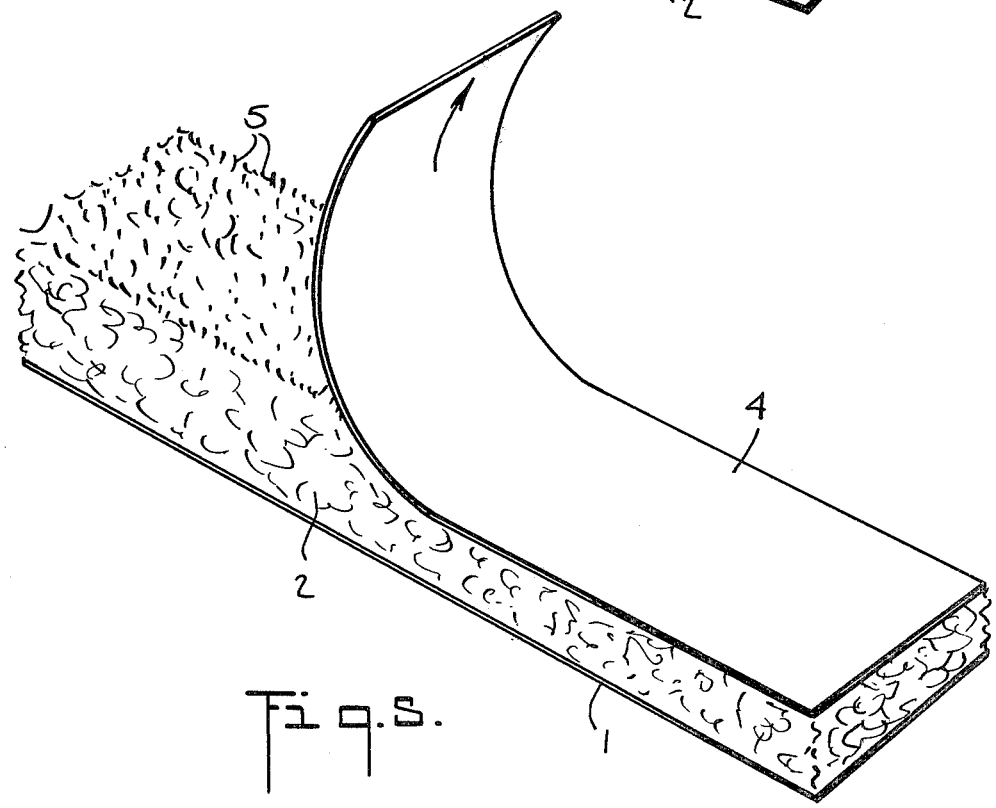
FIG. 5 is like FIG. 4 but shows the fluffing action involved when the inner layer is pulled away from the filter to prepare the filter for use.

The new anal filter, when using the inner or fluffy layer is shown by FIGS. 4 and 5 where the inner layer is indicated at 4.

The fibrous material 2 should be firmly and permanently fixed to the outer layer 1 which is a permanent part of the filter. This may be effected by the use of suitable adhesive used in adequate amount. However, the inner layer 4 should be fixed to the inner surface of the fibrous layer 2 by an adhesive, which may be a pressure-sensitive adhesive, which permits the inner layer 4 to be pulled away, as indicated by FIG. 5. While at the same time pulling upwardly or outwardly the individual fibers, indicated at 5, of the fibrous material 2. Adhesives of other types may be used providing the inner layer or fluffy cover 4 is fixed mainly to the surface fibers of the material 2, in which case the individual fibers are pulled outwardly until they rupture or break, the effect again being a fluffing up of the individual fibers of the fibrous material.

The showing of FIG. 4 serves to illustrate how the new anal filter can be made into a merchandisable unit of which a number can be stacked and packaged, preferably under sterile conditions. One or more of the units can be easily carried by the user without fear of contamination of the working or active surface of the fibrous material 2, keeping in mind that this material is preferably sterile absorbant cotton.

In connection with the above it is preferable that the inner surface of the inner or protective or packaging layer 4, which automatically produces the fluffing action when pulled away, also be sterile, and that the adhesive used to fasten the layer 4 to the material 2 be itself sterile. In any event, the adhesive used should be such that when the layer 4 is peeled away, none of the adhesive remains on the inner or active surface of the material 2. If the layer 4 is adhesively secured permanently, but lightly to the very outermost surface of the material 4, so that when the layer 4 is peeled or pulled away, all of the adhesive and very short broken ends of the fibers 5 remain on the layer 4, there can be no chance for the sterile characteristic of the material 2 being affected.

However, keeping in mind that toilet paper is ordinarily exposed freely to the atmosphere, often for long periods of time, and is, therefore, far from sterile in the medical sense, it may not always be necessary to provide the new anal filter with a completely sterile condition. Toilet paper is freely used with little effect on the user; for many purposes, this new anal filter need be no more sterile than toilet paper.

What is claimed is:

1. An anal filter for attachment to a person's anus and comprising a base layer of porous flexible material to which a fluffy non-woven fibrous layer is attached, said fibrous layer having an outer side attached to said material and an inward surface which is uncovered and exposed, said filter having a length sufficient to transversely extend over the anus and adjacent portions of the person's buttocks and having a width at least sufficient to cover the anus in a vertical direction, said filter being easily flexible under finger pressure so that the filter can be laid with the fibrous layer inward transversely between the buttocks and pressed inwardly by finger pressure so that, by bending, a generally central portion of said inward surface of the fibrous layer contacts the outside of the anus with the balance of said inward surface contacting the adjacent portions of the buttocks, said uncovered and exposed inward surface of said fibrous layer being fluffy to a degree holding the filter on the anus solely by adherence thereto and to said buttock portions without adhesives or insertion into the anus, said filter being pervious to the discharge of gas through the anus but substantially impervious to complete passage of excreta carried by the gas or remaining on the anus from a bowel movement prior to the attachment of the anal filter, and in which said fibrous layer is formed by individual fibers and a covering layer is adhesively fastened temporarily to the inward surface of the fibrous layer, said covering layer being adapted to be pulled free from said fibrous layer prior to use of the anal filter so that said fibers are pulled outwardly while said covering layer is pulled free from the fibrous layer, the inward surface of said fibrous layer being thereby made fluffy to said degree.

* * * * *